United States Patent [19]

Yamada et al.

[11] 4,450,065
[45] May 22, 1984

[54] OXYGEN SENSOR

[75] Inventors: Tetsusyo Yamada; Yutaka Nakayama, both of Nagoya, Japan

[73] Assignee: NGK Spark Plug Co., Ltd., Nagoya, Japan

[21] Appl. No.: 402,071

[22] Filed: Jul. 26, 1982

[30] Foreign Application Priority Data

Mar. 9, 1982 [JP] Japan .................. 57-36973

[51] Int. Cl.$^3$ ........................... G01N 27/58
[52] U.S. Cl. .................. 204/412; 204/425; 204/426
[58] Field of Search .......... 204/425, 426, 1 S, 412, 204/410; 422/94, 95, 96, 97; 123/489; 60/276

[56] References Cited

U.S. PATENT DOCUMENTS 4,272,329  6/1981  Hetrick et al. ................. 204/1 T

FOREIGN PATENT DOCUMENTS 56-130649  1/1981  Japan ................. 204/1 T

*Primary Examiner*—G. L. Kaplan
*Attorney, Agent, or Firm*—Fleit, Jacobson, Cohn & Price

[57] ABSTRACT

The disclosed oxygen sensor has a plate-like oxygen pump element with electrodes, a plate-like oxygen concentration cell element with electrodes, and a means to couple the two elements in parallel to each other while forming a gap between those electrodes of the two elements which face with each other, so that the oxygen concentration cell element measures a ratio between oxygen concentration in said gap and oxygen concentration of a gas surrounding outside of the oxygen sensor, while said oxygen pump element causes diffusion of oxygen between said gap and the outside of the oxygen sensor.

9 Claims, 6 Drawing Figures

OXYGEN SENSOR

BACKGROUND OF THE INVENTION

1. Field of the Invention

This invention relates to an oxygen sensor for measuring oxygen concentration in a gas such as an exhaust gas, and more particularly to an oxygen sensor which can accurately determine air-fuel ratio or the like of a gas being measured with a comparatively low dependence on temperature.

2. Description of the Prior Art

To improve fuel cost and cleanness of exhaust gas of an automobile engine, it has been proposed to run the engine with an intake air-fuel mixture of lean burn side, i.e., with an air-fuel ratio λ, or an excess air ratio, larger than the theoretical optimal value at unity ($\lambda = 1$). To this end, there is a need for an oxygen sensor which can accurately measure the air-fuel ratio of unity or larger than unity $\lambda \geq 1$. One example of such oxygen sensors of the prior art was disclosed in Japanese Patent Laying-open Publication No. 130,649/81 which was filed by the Ford Motor Company of the U.S.A.

The above-mentioned Ford's oxygen sensor uses two sintered plates of oxygen-ion-conductive solid electrolyte each of which has electrodes attached to opposite surfaces thereof. One of the sintered plates is used as an oxygen pump element while the other one of them is used as an oxygen concentration cell element. The oxygen pump element and the oxygen concentration cell element are attached to opposite surfaces of a cylindrical spacer so as to sandwich the sidewall of the cylindrical spacer by the two elements. The sidewall of the cylindrical spacer is made of a refractory material and has fine holes bored therein, so that an enclosed space is defined between the above-mentioned two elements while oxygen-diffusing holes are defined by said fine holes of the sidewall of the cylindrical spacer. The oxygen concentration of a gas can be electrically measured by placing the oxygen sensor in the gas, and applying an electric current through the oxygen pump element so as to pump out the oxygen from the above-mentioned enclosed space to the outside atmosphere or the gas being measured, while allowing diffusion of oxygen into the enclosed space through the oxygen-diffusing holes of the cylindrical spacer sidewall, until for instance an oxygen concentration ratio between the enclosed space and the outside atmosphere of the gas being measured reaches a certain stable value. The last mentioned oxygen concentration ratio is given by the oxygen concentration cell element as an output thereof, and the magnitude of the current applied to the oxygen pump element for pumping out oxygen corresponds to the oxygen concentration in the outside atmosphere of the gas being measured. This oxygen sensor uses the oxygen pump element and the oxygen concentration cell element which are separately formed, so that the output from the oxygen sensor has an advantage in that the dependence of the output thereof on the temperature of the outside atmosphere of the gas being measured, namely the temperature of the oxygen sensor, is low. However, the above oxygen sensor of the prior art has shortcomings in that its response characteristics are not good because the oxygen-diffusing holes of the cylindrical spacer sidewall carrying the two elements are comparatively very small relative to the volume of the enclosed space, and that the oxygen diffusing-holes are apt to be contracted or plugged by deposits from the gas being measured such as automobile engine exhaust gas. Accordingly, accurate measurement of the oxygen concentration was often impossible due to such concentration or plugging of the oxygen-diffusing holes. Even if the oxygen-diffusing holes are not plugged, slight deposits have proved to seriously affect the efficiency of the oxygen diffusion into the enclosed space because the diameter of such oxygen-diffusing holes is very small. Thus, the accuracy in the oxygen concentration measurement is easily deteriorated by the deposits.

SUMMARY OF THE INVENTION

Therefore, an object of the present invention is to obviate the above-mentioned shortcomings of the oxygen sensors of the prior art such as the conventional oxygen sensor for measuring the air-fuel ratio, and to provide a novel oxygen sensor of simple construction which sensor has excellent response characteristics and a high accuracy of measurement, based on the outcome of a series of studies carried out by the inventors.

To fulfil the object, an oxygen sensor according to the present invention comprises an oxygen pump element having a first oxygen-ion-conductive solid electrolyte board with electrode layers attached to opposite surfaces at one end of the first board, an oxygen concentration cell element having a second oxygen-ion-conductive solid electrolyte board with electrode layers attached to opposite surfaces at one end of the second board, and a means for coupling said oxygen pump element and said oxygen concentration cell element in parallel to each other with a gap formed between the electrodes attached to the opposing surfaces of the first board and the second board, whereby said oxygen concentration cell element generates electromotive force caused by the difference between oxygen concentration in said gap and oxygen concentration of a gas surrounding outside of the oxygen sensor while said oxygen pump element performs oxygen transportation therethrough from said gap to the outside of the oxygen sensor.

BRIEF DESCRIPTION OF THE DRAWINGS

For a better understanding of the invention, reference is made to the accompanying drawing, in which.

Throughout different views of the drawings, 1 is an oxygen sensor, 2 is an oxygen pump element, 3 is an oxygen concentration cell element, 2c and 3c are oxygen-ion-conductive solid electrolyte boards, 4 through 7 are electrodes, 8 is an adhesive layer, 9 is a gap, and 10 and 11 are heater elements.

DESCRIPTION OF THE PREFERRED EMBODIMENTS

Figure 1:
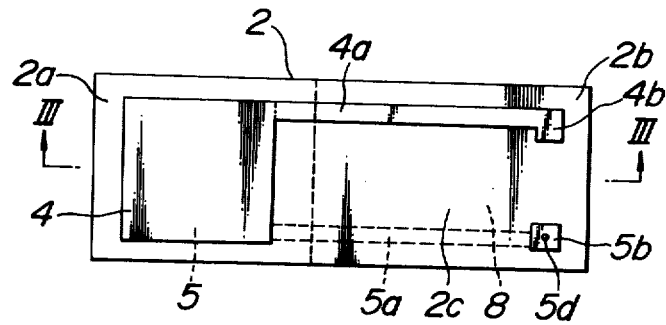
FIG. 1 is a plan view of a first embodiment of the oxygen sensor according to the present invention, as seen from the direction of the arrow I of FIG. 4.
Figure 2:
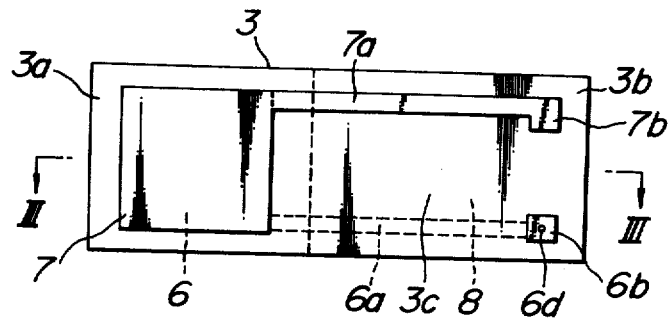
FIG. 2 is a rear view of the embodiment of FIG. 1, as seen from the direction of the arrow II of FIG. 4.
Figure 3A:
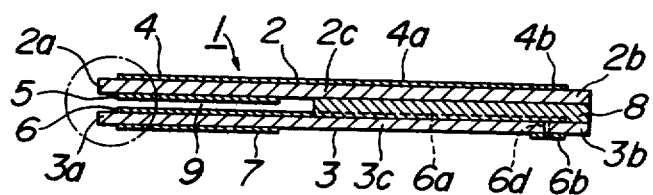
FIG. 3A is a sectional view taken along the line III—III of FIG. 2.

Referring to FIG. 1, FIG. 2 and FIG. 3A, an oxygen sensor 1 in the first embodiment of the present invention has an oxygen pump element 2. The main body of the oxygen pump element 2 is an oxygen-ion-conductive solid electrolyte board 2c which is a rectangular sintered member. Electrodes 4 and 5 are attached to opposite surfaces of the solid electrolyte board 2c at front portion 2a thereof, so that the electrodes 4 and 5 are disposed back to back across the solid electrolyte board 2c. In the illustrated embodiment, the electrodes 4 and 5 are square heat-resisting porous metallic layers which are deposited on the solid electrolyte board 2c by a conventional porous layer depositing method, while leaving fringe setbacks by keeping suitable width of the solid electrolyte board 2c uncovered by the electrodes 4 and 5 along the three side edges thereof.

A lead wire 4a made of a heat-resisting metallic strap layer extends straight from one corner of the square electrode 4 along the rear side thereof toward the rear portion 2b of the solid electrolyte board 2c. A similar lead wire 5a made of a heat-resisting metallic strap layer extends straight from one corner of the other square electrode 5 along the rear side thereof toward the rear portion 2b of the board 2c. The two lead wires 4a and 5a emanate from opposite ends of the rear sides of the electrodes 4 and 5 as shown in FIG. 1. An outlet portion 4b is formed at the rear end of the lead wire 4a at the rear portion 2b of the solid electrolyte board 2c as shown in FIG. 1. The rear end of the other lead wire 5a is electrically connected to an outlet portion 5b formed on the opposite side surface of the solid electrolyte board 2c across a through hole 5d at the rear portion 2b thereof, as shown in FIG. 1. Consequently, the outlet portions 4b and 5b for the two electrodes 4 and 5 are both disposed on the same surface of the solid electrolyte board 2c.

The oxygen concentration cell element 3 is formed in a manner similar to the oxygen pump element 2. More particularly, the main body of the oxygen concentration cell element 3 is an oxygen-ion-conductive solid electrolyte board 3c which is a rectangular sintered member having substantially the same dimensions as those of the solid electrolyte board 2c of the oxygen pump element 2. Square electrodes 6 and 7 made of heat-resisting porous metallic layers are attached to the opposite surfaces of the solid electrolyte board 3c at the front portion 3a thereof in a manner similar to the electrodes 4 and 5 of the oxygen pump element 2. A lead wire 6a made of a heat-resisting metallic strap layer extends straight from one corner of the square electrode 6 along the rear side thereof toward the rear portion 3b of the solid electrolyte board 3c. A similar lead wire 7a made of a heat-resisting metallic strap layer extends straight from one corner of the other square electrode 7 along the rear side thereof toward the rear portion 3b of the board 3c. The lead wires 6a and 7a emanate from opposite ends of the rear sides of the electrodes 6 and 7 as shown in FIG. 2. An outlet portion 7b is formed at the rear end of the lead wire 7a at the rear portion 3b of the solid electrolyte board 3c as shown in FIG. 2. The rear end of the lead wire 6a is electrically connected to an outlet portion 6b formed on the opposite side surface of the solid electrolyte board 3c across a through hole 6d bored at the rear portion 3b thereof, as shown in FIG. 2. Consequently, the outlet portions 6b and 7b for the two electrodes 6 and 7 are both disposed on the same surface of the solid electrolyte board 3c.

The solid electrolyte boards 2c and 3c of the oxygen pump element 2 and the oxygen concentration cell element 3 are required to be oxygen-ion-conductive. Typical materials of the solid electrolyte boards 2c and 3c are solid solutions of zirconia with either yttria or calcia. Other oxygen-ion-conductive solid electrolytes which can be used in the present invention are solid solutions of cerium dioxide, thorium dioxide or hafnium dioxide; solid solutions of perovskite type oxides; and solid solutions of oxides of trivalent metals. The inventors used zirconia partially stabilized by 2-3 yttrium dioxide for the solid electrolyte boards 2c and 3c.

Heat-resisting metallic layers are used to form the electrodes 4, 5, 6 and 7, the lead wires 4a, 5a, 6a and 7a, and the outlet portions 4b, 5b, 6b and 7b on the surfaces of each of the solid electrolyte boards. The inventors used a paste of platinum (Pt), ruthenium (Ru), palladium (Pd), rhodium (Rh), iridium (Ir), gold (Au) or silver (Ag) to print the circuits of the electrodes, lead wires and outlet portions, and the thus printed circuits were sintered to produce the oxygen pump element 2 and the oxygen concentration cell element 3. Instead, such metallic layers may be attached to the solid electrolyte boards by frame spraying, chemical plating, or vacuum evaporation. Porous protective layers of alumina, spinel or the like may be applied to the surfaces of the above-mentioned electrodes.

Although the oxygen pump element 2 and the oxygen concentration cell element 3 may be produced one by one, it is advantageous from the standpoint of productivity to simultaneously print metallic layers of the electrodes and the like for a plurality of such elements on a large green ceramic sheet of the solid electrolyte before sintering, and then to cut the individual elements for baking the individual elements.

Figure 4:
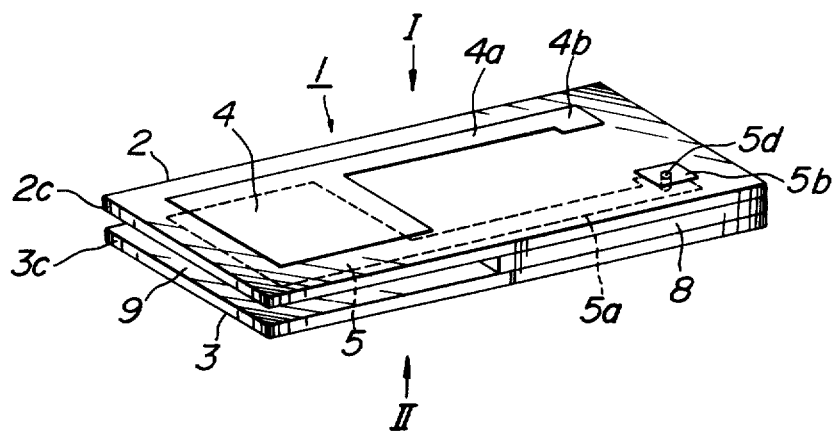
FIG. 4 is a perspective view of the first embodiment of the oxygen sensor of the invention.

Rear portions 2b and 3b of the oxygen pump element 2 and the oxygen concentration cell element 3 are coupled by an adhesive layer 8 such as a heat-resisting inorganic adhesive layer, while holding the elements 2 and 3 in parallel to each other, so that an oxygen sensor 1 with a certain gap 9 between the electrodes 5 and 6 is assembled as shown in FIG. 3A and FIG. 4.

To couple the two elements 2 and 3 in parallel to each other with a certain gap therebetween, the following method may be used; namely, a suitable amount of heat-resisting inorganic adhesive such as a ceramic adhesive is applied to the rear portion 2b or 3b of one of the two elements 2 and 3, and a spacer with a uniform thickness consisting of one or more sheets of gauge, paper, vinyl membrane or aluminium foil with an individual sheet thickness of 0.01-0.05 mm is inserted between the front portions 2a and 3a of the two elements 2 and 3, which elements are then pressed toward each other, whereby the adhesive is spread to the entire rear portions 2b and 3b of the two elements 2 and 3. After excess adhesive projecting to the outside of the two elements 2 and 3 is removed, the thus coupled elements 2 and 3 are heated to solidify the adhesive layer 8.

Figure 3B:
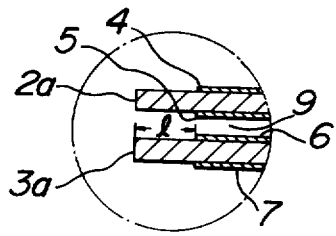
FIG. 3B is a fragmentary sectional view of the first embodiment of a somewhat larger scale than that of FIG. 3A.

The magnitude of the gap 9 between the oxygen pump element 2 and the oxygen concentration cell element 3 depends on the shape of the elements, the areas of the electrodes, and the magnitude of the output of the oxygen concentration cell element 3. For instance, when each of the electrodes 4, 5, 6 and 7 is square with an area of 100 mm$^2$ and has a fringe setback l (see FIG. 3B) of 0.5-3.0 mm between the outer edges of the solid electrolyte boards 2c or 3c and the outer edges of the electrodes 4, 5, 6 or 7, the gap 9 can be 0.01-0.5 mm. When the electric current through the oxygen pump element 2 is comparatively large in the range of 1-100 mA, the gap 9 may be made somewhat larger, while when the electric current through the oxygen pump element 2 is comparatively small in the range of 0.1-10 mA, the gap 9 can be made somewhat smaller. Thus, the gap 9 can be adjusted depending on the requirements of specific use. The output range of the electric current of the oxygen pump element 1 is for detecting the oxygen density of about 0.1-10% under the condition that the output of the oxygen concentration cell element 3 is held at a preselected constant level as is described later. Accordingly, the oxygen sensor of the present invention has an advantage in that the magnitude of the gap 9 between the oxygen pump element 2 and the oxygen concentration cell element 3 can be easily adjusted simply by modifying the thickness of the above-mentioned spacer, whereby the electric current through the oxygen pump element 2 can be easily modified to its optimal value.

The operation of the oxygen sensor according to the present invention in measuring the air-fuel ratio is for instance as follows:

The oxygen sensor 1 of FIGS. 1 through 4 is placed in a gas to be measured, and a DC voltage is applied across the oxygen pump element 2, e.g., a positive potential to the outer electrode 4 while a negative potential to the inner electrode 5. Thus, oxygen ions move through the solid electrolyte board 2c of the oxygen pump element 2 from the inner electrode 5 to the outer electrode 4, so that oxygen is pumped out from the gap 9 between the two elements 2 and 3 to the outside of the oxygen pump element 2.

As the oxygen is pumped out of the gap 9 as described above, a difference is produced between the oxygen concentration in the gap 9 and the oxygen concentration in the ambient atmosphere outside the oxygen concentration cell element 3. This difference in the oxygen concentration generates an electromotive force E across the oxygen concentration cell element 3, which electromotive force E in this case will be given by the following Nernst equation.

$$E = (RT/4F) \cdot \ln Pc/Pa$$

Here,

Pc: oxygen partial pressure in the outside atmosphere or a gas being measured,
Pa: effective average oxygen partial pressure in the gap 9,
R: the gas constant,
T: absolute temperature, and
F: the Faraday constant.

The electromotive force E of the oxygen concentration cell element 3 quickly reaches a constant level as a balance is quickly reached between the incoming amount of oxygen into the gap 9 of the oxygen sensor 1 through openings along the three sides thereof and the outgoing amount of oxygen being pumped out of the gap 9 to the outside of the oxygen sensor 1 by the oxygen pump element 2. When the electric current through the oxygen pump element 2 is adjusted so that the electromotive force E of the oxygen concentration cell element 3 is held at a certain preselected level, then the magnitude of the thus adjusted electric current is substantially linearly proportional to the contents or concentration oxygen in the outside atmosphere or the gas being measured, provided that the temperature is approximately constant. Upon processing the data representing the magnitude of the electric current and the related temperature compensation, the oxygen concentration in the outside atmosphere or the gas being measured can be determined with a good response characteristic to any variations of the oxygen concentration.

When the oxygen sensor 1 of the invention is used for measuring the oxygen concentration in the automobile engine exhaust gas, even if carbon particles or mist substances of the exhaust gas deposit on certain localized portions of the oxygen sensor 1, the oxygen diffusion in the oxygen sensor 1 of the invention is hardly affected by such deposits as one of the salient features of the invention, because the gap 9 has openings along the three sides thereof for allowing the incoming diffusion of oxygen thereto. Thus, measuring accuracy of the oxygen sensor 1 of the present invention is hardly affected by such deposits.

Figure 5:
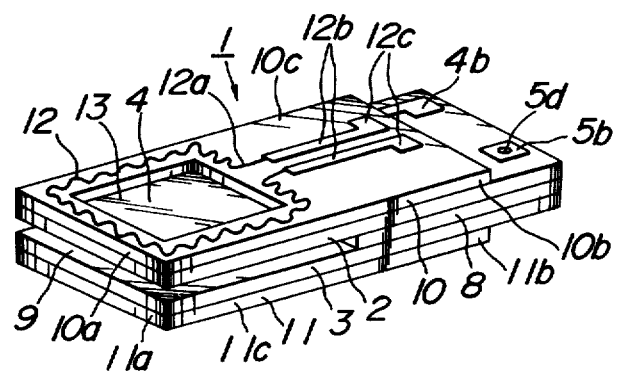
FIG. 5 is a perspective view of a second embodiment of the oxygen sensor of the present invention.

FIG. 5 shows a second embodiment of the oxygen sensor according to the present invention. The second embodiment has heater elements 10 and 11 added to the oxygen sensor of the first embodiment.

Main bodies of the heater elements 10 and 11 are electrically insulating inorganic plates 10c and 11c, which are rectangular alumina or spinel plates with a length shorter than the overall length of the oxygen sensor 1. A hole 13 is bored through each of the insulating plates 10c and 11c at the front portion 10a or 11a thereof. The positions and the sizes of the holes 13 are such that substantially the entire electrodes 4 and 7 are exposed to the outside of the oxygen sensor 1 through the holes 13, as can be seen from FIG. 5. The insulating plates 10c and 11c have heat-generating wires 12 disposed therein along the peripheral walls of the holes 13. In the illustrated embodiment of FIG. 5, the heat-generating resistors 12 is bent in a waved form in the proximity of the hole 13, and the two end portions 12a of the resistor 12 are connected to two lead wires 12b. The lead wires 12b extend to the rear portion 10b or 11b of the insulating plate 10c or 11c where outlet portions 12c are formed at the rear ends of the lead wires 12b. The heat-generating resistors 12, the lead wires 12b, and the outlet portions 12c are made of heat-resisting metallic layers. For instance, the heat-generating resistors 12 are formed by printing with a paste of heat-resisting metal such as platinum (Pt) or gold (Au), while the lead wires 12b and the outlet portions 12c are formed by printing with a past of heat-resisting metal which is most commonly platinum (Pt). When the heat-generating wires 12 and the lead wires 12b are designed to be embedded in a ceramic plate, they can be formed by printing a metal with a high melting point such as tungsten.

The above heater elements 10 and 11 are attached to a green body of the oxygen sensor 1 of the first embodiment while aligning the front portions thereof and then sintered so as to integrally couple the heater elements 10 and 11 to the oxygen sensor 1. Instead, the heater elements 10 and 11 may be adhered to the oxygen sensor 1 after sintering. Whereby, the oxygen sensor 1 of the second embodiment is assembled.

In operation, an electric current is applied to the heat-generating resistor 12 through the outlet portions 12c and the lead wires 12b, so as to heat the oxygen sensor 1. Accordingly, the overall temperature of the oxygen sensor 1 can be controlled by adjusting the magnitude of the current through the heat-generating resistors 12. When the temperature of the gas being measured is low, the two elements, especially the oxygen pump element, of the oxygen sensor 1 is heated to promote the activities thereof. Besides, the heating by the heat-generating resistors 12 gives temperature compensation during the measurement, so as to improve the preciseness and the accuracy of the measurement.

Typical dimension the oxygen pump element 2, the oxyten concentration cell element 3 and the heater element 10 or 11, respectively, are 5–70 mm in length, 3–10 mm in width, and about 0.5 mm in thickness for regular applications.

In short, the oxygen sensor of the present invention measures the oxygen partial pressure in the gas or atmosphere being measured based on the fact that, when a steady balance of the oxygen flow and a steady distribution of the oxygen concentrations are established in the oxygen sensor, there is a functional relationship among the oxygen partial pressure in the gas being measured, the electric current through the oxygen pump element for pumping in or pumping out (this current directly relates to the amount of oxygen transportation from the above-mentioned gap space to the gas being measured or vice versa through the oxygen pump element), and the output from the oxygen concentration cell element, which output results from the difference between the induced oxygen partial pressure in the above-mentioned space or the enclosed space communicating with the gas being measured through the above-mentioned openings and the oxygen partial pressure in the gas being measured. Accordingly, the method of the measurement by using the oxygen sensor of the invention is not restricted to the above-mentioned approach of varying the magnitude of the electric current through the oxygen pump element, but the oxygen sensor of the invention can be used by a different method, for instance by allowing the output from the oxygen concentration cell element to vary so as to represent the oxygen partial pressure of the gas being measured under the conditions that the pumping out electric current through the oxygen pump element is controlled at a constant value.

As described in the foregoing, the oxygen sensor according to the present invention uses two oxygen-ion-conductive solid electrolyte boards coupled together at rear ends thereof so that the two boards extend in parallel to each other with a gap between front portions thereof, each of said boards having two electrodes attached to opposite surfaces thereof at the front portion thereof, one of said two solid electrolyte boards forming an oxygen pump element while the other solid electrolyte board forming an oxygen concentration cell element which output results from the induced oxygen concentration difference between said gap and the atmosphere or gas surrounding the oxygen sensor. Thus, the gap between the electrodes of the two elements of the oxygen sensor is open along three sides thereof for allowing the incoming diffusion of oxygen therethrough, so that the time necessary for the oxygen diffusion is shortened. Besides, when the oxygen sensor is used to measure the oxygen concentration of automobile engine exhaust gas or other exhaust gas, even if deposits are precipitated on the oxygen sensor from the exhaust gas, the large inlet opening of the gap of the oxygen sensor along the three sides thereof ensures that the incoming oxygen diffusion into the gap is hardly affected by such deposits, so that precise and accurate measurement of the oxygen concentration is ensured over a long period of service life of the oxygen sensor. The oxygen sensor of the present invention is simple in construction, so that the oxygen sensor can be manufactured easily with comparatively simple quality control efforts. Further, design modifications, especially modifications of the magnitude of the gap, can be easily effected, so that either input or output power of the two elements of the oxygen sensor can be easily adjusted. Accordingly, the oxygen sensor of the present invention has an advantage in that it can be easily applied to various industrial fields.

Although the present invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An oxygen sensor, comprising an oxygen pump element having a first oxygen-ion-conductive solid electrolyte board with electrode layers attached to opposite surfaces at one end of the first board, an oxygen concentration cell element having a second oxygen-ion-conductive solid electrolyte board with electrode layers attached to opposite surfaces at one end of the second board, and a means for coupling said oxygen pump element and said oxygen concentration cell element in parallel to each other with a gap between the electrode layers attached to the opposing surfaces of the first board and the second board, the edges of said gap being open to the surrounding atmosphere along at least three sides thereof, whereby said oxygen concentration cell element generates electromotive force caused by the difference between oxygen concentration in said gap and oxygen concentration of a gas surrounding the outside of the oxygen sensor while said oxygen pump element performs oxygen transportation therethrough from said gap to the outside of the oxygen sensor or vice versa to cause said oxygen concentration difference therebetween.

2. An oxygen sensor as set forth in claim 1, wherein said means for coupling is an adhesive layer consisting of a heat-resisting inorganic adhesive.

3. An oxygen sensor as set forth in claim 1, wherein said first and second oxygen-ion-conductive solid electrolyte boards are made of solid electrolyte selected from the group consisting of solid solutions of zirconia and yttria, solid solutions of zirconia and calcia, solid solutions of cerium dioxide, solid solutions of thorium dioxide, solid solutions of hafnium dioxide, solid solutions of perovskite type oxides, and solid solutions of oxides of trivalent metals.

4. An oxygen sensor as set forth in claim 1, wherein said electrode layers are made of heat-resisting metallic layers made of at least one metal selected from the group consisting of platinum (Pt), ruthenium (Ru), palladium (Pd), rhodium (Rh), iridium (Ir), gold (Au) and silver (Ag).

5. An oxygen sensor as set forth in claim 1, wherein said gap is 0.01–0.5 mm wide.

6. An oxygen sensor as set forth in claim 1, wherein said gap is substantially square and has one side thereof closed by said means for coupling and three sides thereof left open.

7. An oxygen sensor comprising an oxygen pump element having a first oxygen-ion-conductive solid electrolyte board with electrode layers attached to opposite surfaces at one end of the first board; an oxygen concentration cell element having a second oxygen-ion-conductive solid electrolyte board with electrode layers attached to opposite surfaces at one end of the second board; a means for coupling said oxygen pump element and said oxygen concentration cell element in parallel to each other with a gap between the electrode layers attached to the opposing surfaces of the first board and the second board, the edges of said gap being open to the surrounding atmosphere along at least three sides thereof; and at least one heater element attached to the outer surface of said oxygen pump element, said heater element having through holes bored at those portions which correspond to the electrode layer of said oxygen pump element, said electrode layer being exposed to the outside of said oxygen sensor through said opening of the heater element, whereby said oxygen concentration cell element generates electromotive force caused by the difference between the oxygen concentration in said gap and the oxygen concentration of a gas surrounding the outside of the oxygen sensor while said oxygen pump element performs oxygen transportation therethrough from said gap to the outside of the oxygen sensor, or vice versa, to cause said oxygen concentration difference therebetween.

8. An oxygen sensor as set forth in claim 7, wherein the heater element has a main body made of an electrically insulating inorganic material selected from the group consisting of alumina and spinel.

9. An oxygen sensor as set forth in claim 7, wherein heater elements are attached to the outer surfaces of said oxygen pump element and said oxygen concentration cell element, said heater elements having through holes bored at those portions which correspond to electrode layers of said oxygen pump element and said oxygen concentration cell element, whereby said electrode layers are exposed to the outside of said oxygen sensor through said openings of the heater elements.

* * * * *